United States Patent
Matsumoto et al.

(10) Patent No.: US 9,470,640 B2
(45) Date of Patent: Oct. 18, 2016

(54) DEFECT INSPECTION METHOD AND DEFECT INSPECTION DEVICE

(71) Applicant: HITACHI HIGH-TECHNOLOGIES CORPORATION, Minato-ku, Tokyo (JP)

(72) Inventors: Shunichi Matsumoto, Tokyo (JP); Atsushi Taniguchi, Tokyo (JP); Toshifumi Honda, Tokyo (JP); Yukihiro Shibata, Tokyo (JP); Yuta Urano, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/042,598

(22) Filed: Feb. 12, 2016

(65) Prior Publication Data

US 2016/0161422 A1    Jun. 9, 2016

Related U.S. Application Data

(63) Continuation of application No. 14/232,929, filed as application No. PCT/JP2012/066561 on Jun. 28, 2012, now Pat. No. 9,291,574.

(30) Foreign Application Priority Data

Sep. 28, 2011    (JP) ................................ 2011-211885

(51) Int. Cl.
*G01N 21/00* (2006.01)
*G01N 21/95* (2006.01)
(Continued)

(52) U.S. Cl.
CPC ........ *G01N 21/9501* (2013.01); *G01N 21/956* (2013.01); *G01N 2201/126* (2013.01); *G01N 2201/127* (2013.01); *H01L 22/12* (2013.01); *H01L 2924/0002* (2013.01)

(58) Field of Classification Search
CPC ..................................................... G01N 21/00

USPC ........................................... 356/237.5, 237.6
See application file for complete search history.

(56) References Cited

U.S. PATENT DOCUMENTS 5,903,342 A    5/1999  Yatsugake et al.
7,535,561 B2*  5/2009  Chikamatsu ....... G01N 21/9501
                                                    356/237.2
(Continued)

FOREIGN PATENT DOCUMENTS

JP    09-304289 A    11/1997
JP    11-264800 A     9/1999
(Continued)

OTHER PUBLICATIONS

Born, M., et al., "Principles of Optics", Cambridge University Press, pp. 774-785, (1999).
(Continued)

*Primary Examiner* — Roy M Punnoose
(74) *Attorney, Agent, or Firm* — Miles & Stockbridge P.C.

(57) ABSTRACT

A defect inspection method and device for irradiating a linear region on a surface-patterned sample mounted on a table, with illumination light from an inclined direction to the sample, next detecting in each of a plurality of directions an image of the light scattered from the sample irradiated with the illumination light, then processing signals obtained by the detection of the images of the scattered light, and thereby detecting a defect present on the sample; wherein the step of detecting the scattered light image in the plural directions is performed through oval shaped lenses in which elevation angles of the optical axes thereof are different from each other, within one plane perpendicular to a plane formed by the normal to the surface of the table on which to mount the sample and the longitudinal direction of the linear region irradiated with the irradiation light.

14 Claims, 13 Drawing Sheets

(51) Int. Cl.
*G01N 21/956* (2006.01)
*H01L 21/66* (2006.01)

(56) References Cited

U.S. PATENT DOCUMENTS

| | | | |
|---|---|---|---|
| 8,699,017 B2* | 4/2014 | Oka | G01N 21/9501 356/237.1 |
| 2002/0036769 A1 | 3/2002 | Shimoda et al. | |
| 2007/0216896 A1 | 9/2007 | Chikamatsu | |
| 2008/0068593 A1* | 3/2008 | Nakano | G01N 21/95607 356/73 |
| 2008/0165343 A1 | 7/2008 | Lewis et al. | |
| 2008/0204736 A1 | 8/2008 | Chikamatsu et al. | |
| 2008/0291436 A1* | 11/2008 | Aiko | G01N 21/9501 356/237.2 |
| 2009/0033924 A1 | 2/2009 | Uto et al. | |
| 2009/0059216 A1 | 3/2009 | Shibata et al. | |
| 2009/0207405 A1 | 8/2009 | Chikamatsu et al. | |
| 2009/0262339 A1 | 10/2009 | Suga et al. | |
| 2010/0271473 A1* | 10/2010 | Aiko | G01N 21/9501 348/92 |
| 2011/0141463 A1 | 6/2011 | Chikamatsu et al. | |
| 2013/0182100 A1* | 7/2013 | Aiko | G01N 21/9501 348/87 |

FOREIGN PATENT DOCUMENTS

| | | |
|---|---|---|
| JP | 2002-090311 A | 3/2002 |
| JP | 2004-177284 A | 6/2004 |
| JP | 2007-524832 A | 8/2007 |
| JP | 2007-248086 A | 9/2007 |
| JP | 2008-241688 A | 10/2007 |
| JP | 2008-249571 A | 10/2008 |
| JP | 2008-261790 A | 10/2008 |
| JP | 2009-053132 A | 3/2009 |
| JP | 2010-054395 A | 3/2010 |

OTHER PUBLICATIONS

Edlen, B., "The Refractive Index of Air", Metrologia, vol. 2, No. 2, pp. 71-80, (1966).
Sellmeier, W., "Zur Erklärung der abnormen Farbenfolge im Spectrum einiger Substanzen," Annalen der Physik und Chemie, pp. 272-282, 1871.

* cited by examiner

DEFECT INSPECTION METHOD AND DEFECT INSPECTION DEVICE

BACKGROUND

The present invention relates generally to inspection techniques that use optically acquired image signal information to detect defects present on a surface-patterned object to be inspected. More particularly, the invention is directed to an inspection technique for detecting microscopic defects present on a patterned substrate such as a semiconductor wafer.

In defect inspection of a substrate having patterns formed on a surface (i.e., a patterned substrate), defect detection sensitivity depends greatly upon how accurately a defect-diffracted/scattered detection beam of light, or a defect signal, can be detected in distinction from pattern-diffracted/scattered and underlayer-diffracted/scattered detection beams of light, or background light noise. During the inspection of a semiconductor wafer, in particular, the detection of even more microscopic defects is being demanded in response to the progress of further microstructured patterning, and how accurately a very weak defect signal from a microscopic defect can be extracted distinctively from background light noise is a big technological challenge associated with defect inspection.

A vertical structure of a patterned substrate, which is an object to be inspected, and the kinds of defects to be detected are described below per FIG. 2, taking a semiconductor wafer as an example. FIG. 2 uses reference numbers 20 to 35 and 201 to 251 to denote the vertical structure of the semiconductor wafer, and uses reference numbers 261 to 264 to denote the kinds of defects to be detected.

Reference number 20 denotes an element isolation layer, and reference number 202 denotes a structure in which, after trenching of a silicon (Si) substrate 201, the trenches are filled in with silicon oxide ($SiO_2$), which is an insulator, to provide electrical insulating separation between transistor elements formed on the wafer. Reference number 21 denotes a gate and contact layer, and reference number 211 denotes gate electrode portions formed from polysilicon (poly-Si). The gate electrode portions are greatly influential upon transistor performance, weighing heavily in defect inspection as well. Reference number 212 denotes contact portions.

Each of the contact portions is where a transistor region and an electrical interconnect layer formed above the transistor region are interconnected via a metal, such as tungsten (W), that is buried in a hole etched in the insulating film (silicon dioxide: $SiO_2$). The interconnect layers 22 to 25 form a circuit. These layers are each filled in with an insulating film such as silicon dioxide ($SiO_2$). Reference number 22 denotes a first interconnect layer, which includes a first interconnect portion 221 for planar interconnection. A first via portion 222 is where the transistor region and an electrical interconnect layer formed further above the transistor region are interconnected via a metal buried in a hole etched in an insulating film such as silicon dioxide ($SiO_2$). Reference number 23 denotes a second interconnect layer, which includes a second interconnect portion 231 and a second via portion 232. Similarly, reference number 24 denotes a third interconnect layer, which includes a third interconnect portion 241 and a third via portion 242. Reference number 25 denotes a fourth interconnect layer, which includes a fourth interconnect portion 251.

The interconnect portion of each interconnect layer is formed from a material including a metal such as aluminum (Al) or copper (Cu). The metal buried in the via portion is formed from tungsten (W), copper (Cu), or the like.

The defects to be detected are, for example, a scratch 261, a short circuit 262 and electrical disconnection 264 that are both a pattern defect, and contamination 263.

FIG. 3 is an explanatory diagram of the steps, materials, and typical defects of each layer of the semiconductor device shown in FIG. 2. The layers of the semiconductor device are formed through various steps. These steps include: the step of depositing the material which forms the layer; the step of forming a resist pattern by lithography; the step of removing the layer-deposited material by etching it along the formed resist pattern; and chemical mechanical polishing (CMP) for planarization.

The materials used in each layer and each fabrication step of the semiconductor device are diverse. The kinds of defects to be detected also vary from step to step; in the deposition step, they may be contamination, in the lithographic step for pattern formation and in the etching step, they may be contamination and pattern defects, and in the CMP step for polishing, they may be contamination and scratches.

As described per FIGS. 2 and 3, patterns of various shapes and materials are involved in semiconductor wafer inspection, and defects of various kinds are detected. Inspection devices are configured so that a plurality of detection parameters can be set to obtain optimal defect detection sensitivity according to the particular shape and material of the pattern or the kind of defect to be detected.

As described in JP-A-1997-304289 and JP-A-2007-524832, for example, semiconductor wafer defect inspection devices of a darkfield optical type that are used to inspect defects and contamination present on a substrate with patterns formed on a surface are constructed to illuminate the substrate from an oblique direction and converge the light scattered from the defects, instead of converging via an objective lens the light regularly reflected from the substrate. These inspection devices are also configured so that the light diffracted/scattered from a pattern or underlayer formed on the substrate will be converged via the objective lens, then intensity-reduced by a polarizing filter and/or a spatial filter, and received by a sensor.

With the above configurations, the defect inspection devices of the darkfield optical type can generate an inspection image with a defect represented explicitly as a luminescent spot against a dark background. Therefore, even if image resolution is too high, that is, a sensor pixel size on the sample substrate surface is too large (but up to 0.3 μm), for a minimum size of defects to be detected, the devices can detect smaller defects, for example of 0.1 μm or less in diameter. Since defect inspection devices of the darkfield optical type have such a feature, they are widely used as high-speed high-sensitivity inspection devices on semiconductor device manufacturing lines.

Semiconductor wafer defect inspection devices of the future will be required to have an ability to detect even more microscopic defects with the progress of further device-pattern microstructuring. To respond to this tendency, the optical systems in the patterned-wafer defect inspection devices of the darkfield optical type need to contain appropriate measures against the following several problems.

One of the problems is how to augment a detection aperture (numerical aperture: NA) of the optical system to detect more efficiently the very weak light scattered from microscopic defects. During patterned-wafer defect inspection, however, it is necessary to detect the defect-scattered light in distinction from the light diffracted/scattered from the patterns or underlayer of the wafer. If the detection aperture is merely augmented, although signal intensity of the defect-scattered light will be increased, noise components of the light diffracted/scattered from the patterns or the underlayer will also increase and detection sensitivity of the defect will be difficult to improve.

To cope with these problems, it is effective to utilize a difference in directionality between the defect-scattered light and the pattern- or underlayer-diffracted/scattered light. More specifically, it is effective to detect scattered light in a widest possible range from a plurality of different directions and conduct defect detection using scattered-light images obtained. For example, JP-A-1997-304289 (Patent Document 1) discloses a technique for inspecting defects by detecting scattered light from a plurality of directions. In addition, JP-A-2007-524832 (Patent Document 2) discloses a technique for inspecting defects using the scattered light acquired by a converging optical system placed in an upward direction and oblique direction of a substrate to be inspected. Furthermore, JP-A-2004-177284 (Patent Document 3) discloses a technique for inspecting defects using scattered-light images acquired by an imaging optical system placed in an upward direction and oblique direction of a substrate to be inspected.

Furthermore, JP-A-2008-241688 (Patent Document 4) discloses a technique used to inspect defects by changing an angle of a reflecting mirror positioned between a substrate to be inspected and a detection optical system placed above the substrate, and thereby acquiring images of scattered light from a plurality of directions.

Furthermore, JP-A-2010-54395 (Patent Document 5) discloses a technique used to inspect defects by placing a plurality of reflecting mirrors between a substrate to be inspected and a detection optical system placed above the substrate, and thereby acquiring images of scattered light from a plurality of directions. Moreover, JP-A-2008-261790 (Patent Document 6) discloses a technique for extending a scattered-light detection range by cutting off two end portions of each of circular lenses and using these lenses as part of a detection optical system for detecting scattered light from a plurality of directions. Besides, JP-A-2009-53132 (Patent Document 7) discloses a technique for inspecting defects by conducting comparative processing of scattered-light images acquired from a plurality of directions.

If detectability of a detection optical system is enhanced in an attempt to detect finer defects, such changes as in ambient temperature and in atmospheric pressure will change imaging performance of the detection optical system, resulting in defect detection sensitivity decreasing. Techniques for improving this problem are described in, for example, JP-A-2002-90311, JP-A-2007-248086, and JP-A-2008-249571 (Patent Documents 8, 9, and 10). The techniques disclosed in Patent Documents 8 and 9 relate to correcting changes in imaging position due to changes in temperature and atmospheric pressure. The technique disclosed in Patent Document 10 relates to controlling an internal temperature of an inspection device.

In connection with a scattered-laser-light detection type of defect inspection, "Principles of Optics" (M. Born, E. Wolf), Cambridge University Press, pp. 774-785, (1999) (Non-Patent Document 1) introduces the fact that intensity of a scattered-light signal from a microscopic object whose diameter or radius is smaller than a wavelength of light decreases inversely with the sixth power of a size of the object and increases in proportion to the fourth power of illumination wavelength.

In addition, the relational expression representing the relationship between changes in ambient temperature and ambient air pressure and a change in the reflective index of air is shown in "The Reflective Index of Air" (Bengt Edlen), Metrologia vol. 2, No. 2, pp. 71-80, (1966) (Non-Patent Document 2).

Furthermore, the relational expression representing the relationship between a change in wavelength and a change in the reflective index of a lens material is shown in "Zur Erklarung der abnormen Farbenfolge im Spectrum einiger Substanzen" (Wolfgang Sellmeier), Annalen der Physik and Chemie, pp. 272-282, (1871) (Non-Patent Document 3).

SUMMARY

As described earlier herein, in darkfield defect inspection of a patterned substrate, defect detection sensitivity depends greatly upon how accurately a defect-diffracted/scattered detection beam of light, or a defect signal, can be detected in distinction from pattern-diffracted/scattered and underlayer-diffracted/scattered detection beams of light, or background light noise. It has also been described earlier herein that discrimination between a defect signal and background light noise is achievable by adopting any one of the techniques utilizing the differences between the scattered beams of light causing the defect signal and the background light noise, that is, the differences in the respective orientations of occurrence and polarization states due to the differences in the shape, material, and other factors of the object causing the scattered light.

In darkfield inspection of a patterned substrate, on the other hand, a detection optical system is constituted by an imaging optical system, an image of the light scattered from the substrate to be inspected is acquired, and this acquired image undergoes processing for defect detection. Accordingly, defect detection sensitivity is greatly dictated by the quality of the scattered-light image acquired. For example, it is necessary, in addition to detecting scattered light from a direction different from the previous one and conducting optical filtering with a spatial filter, a polarizing filter, or the like, to construct the optical system so that the image of the scattered light will have the quality needed to discriminate between a defect signal and background light noise.

As described earlier herein, to improve defect detection sensitivity, it is effective to increase the amount of information for defect detection, by detecting defects with a plurality of detection optical systems and acquiring, from one position of one object to be inspected, a plurality of scattered-light images different in features and characteristics. During image processing, in particular, it is effective not only to process each of the scattered-light images independently, but also to conduct comparisons between the scattered-light images different in features and characteristics. In addition, realizing this requires improving the quality of the scattered-light images acquired by the detection optical systems, and minimizing any differences in quality between the scattered-light images acquired by the detection optical systems.

A challenge to be attained by the present invention is to realize the above-described two requirements relating to the improvement of defect detection sensitivity by comparative analysis of a plurality of scattered-light images different in features and characteristics, that is, (a) improving the quality of scattered-light images acquired by a plurality of detection optical systems, and (b) minimizing the differences in quality between the scattered-light images acquired by the detection optical systems.

The inventions described in Patent Documents 1 to 7 relate to techniques for improving defect detection sensitivity by using an appropriate detection optical system according to the direction in which light is scattered, and the invention in Patent Document 1 only detects the amount of light scattered and does not presuppose image acquisition. At least the invention in Patent Document 1 is therefore considered to be unable to meet the challenge that the technique of the present invention is to attain.

The inventions described in Patent Documents 2 and 3 do not presuppose conducting comparisons between a plurality of scattered-light images different in features and characteristics, and are thus considered to be unable to meet the challenge that the technique of the present invention is to attain.

In the inventions according to Patent Documents 4 and 5, when a plurality of kinds of scattered-light images different in detection direction are acquired, the detection optical system to be used is changed in configuration, which causes differences in quality between the plurality of kinds of scattered-light images. For this reason, the inventions described in Patent Documents 4, 5 are considered to be unable to meet the challenge that the technique of the present invention is to attain.

In the invention according to Patent Document 6 is disclosed a technique that relates to avoiding mutual interference of light between a plurality of detection optical systems arranged in different directions, and the technique uses a plurality of circular lenses whose portions that are likely to cause the mutual interference of light are cut off. The particular technique, however, does not envisage ensuring the quality of the scattered-light images obtained when the substrate to be inspected is detected from an oblique direction, so the technique is considered to be unable to meet the challenge that the technique of the present invention is to attain.

The invention described in Patent Document 7 relates to a method of detecting defects by arranging a plurality of detection optical systems in different directions, detecting images different in scattering direction, and comparing the images, or a method of detecting defects by detecting scattered light with a detection optical system having a large NA value of at least 0.7, then branching an optical path and detecting images different in scattering direction, and comparing the images. When a plurality of detection optical systems are arranged in different directions, however, contention for a mounting space (i.e., the possible interference of light) between the plurality of detection optical systems will usually make it difficult to ensure a large detection aperture. In the detection optical system with the large NA value of at least 0.7, it is also difficult, in terms of lens design, to ensure a long working distance (W.D.) between the lens end and the object to be inspected. This means that in the darkfield optical type of defect inspection, in particular, it is difficult to realize a configuration needed to ensure the space for guiding laser illumination light (see FIG. 4) to the wafer surface. In addition, the above invention does not envisage ensuring the quality of the scattered-light images obtained when the substrate to be inspected is detected from an oblique direction, so the technique is considered to be unable to meet the challenge that the technique of the present invention is to attain.

The inventions described in Patent Documents 8 to 10 relate to techniques for accommodating changes in imaging characteristics due to ambient environmental changes, and the inventions in Patent Documents 8, 9 only conduct corrections for in-focus position variations due to the ambient environmental changes, and do not allow for other changes in characteristics, so the corresponding techniques are considered to be unable to meet the challenge that the technique of the present invention is to attain. The invention described in Patent Document 10 only holds a constant temperature environment and does not allow for changes in atmospheric pressure, so the invention is considered to be unable to meet the challenge that the technique of the present invention is to attain.

The present invention contemplates the improvement of defect detection sensitivity, based on comparative analysis of a plurality of scattered-light images different in features and characteristics, and an object of the invention is to provide a defect inspection method and defect inspection device that enables the improvement of quality of scattered-light images acquired by a plurality of detection optical systems, and the minimization of any differences in quality between the scattered-light images acquired by the detection optical systems.

The present invention includes a plurality of means to solve the problems. Among these means is a defect inspection method, which includes: an illumination step of irradiating a surface-patterned object to be inspected, with light from an illumination optical system in such a way as to form a linear illumination region on the surface of the object; a detection step of converging via a detection optical system the light reflected/scattered from the object, then forming an optical image of the object surface on an image sensor, and converting the reflected/scattered light into an electrical signal; a defect discrimination step of extracting a defect signal by processing the electrical signal that has been obtained by the photo-electric conversion; and a scanning step of moving the object in a mounted condition and applying the detection step to the entire surface of the object. The detection step is conducted using a plurality of detection optical systems and image sensors, and the defect discrimination step is conducted to extract the defect signal by comparing detection images obtained by the plurality of detection optical systems and image sensors. The detection optical systems used in the detection step have the same construction and are arranged so that respective optical axes form different angles of elevation in one plane perpendicular to a surface formed and defined by a longitudinal direction of the linear illumination region and a line normal to the object surface; detection lenses used in the detection optical systems are composite lens assemblies, part of which include oval shaped lenses of a left-right symmetrical shape created by cutting off left and right end portions of a circular lens rectilinearly, and rectilinear portions of the detection lenses are disposed to be perpendicular to a surface formed by the optical axes of the detection optical systems; in the illumination step, the longitudinal direction of the linear illumination region is formed to be perpendicular to the optical axes of the detection optical systems; and in the scanning step, scanning is conducted in a direction perpendicular to the longitudinal direction of the linear illumination region.

Another example that the present invention provides as the means for solving the problems is a defect inspection method, which includes: irradiating a linear region on a surface-patterned sample mounted on a table which moves in a plane, with illumination light from an inclined direction relative to a direction of a line normal to the sample; detecting from each of a plurality of directions an image of scattered light originating from the sample irradiated with the illumination light; and detecting a defect on the sample by processing signals obtained by the detection of the images of the scattered light. The step of detecting the scattered light image in the plural directions is performed through oval shaped lenses in which elevation angles of the optical axes thereof are different from each other, within one plane perpendicular to a plane formed by the normal to the surface of the table on which to mount the sample and the longitudinal direction of the linear region irradiated with the irradiation light, the oval shaped lenses being formed of circular lenses having left and right portions thereof cut.

Yet another example that the present invention provides as the means for solving the problems is a defect inspection device, which includes: a table unit adapted to move in a plane with a surface-patterned sample mounted on the table unit; an illumination optics unit that irradiates a linear region on the sample mounted on the table unit, with illumination light from an inclined direction relative to a direction of a line normal to the patterned surface of the sample; a detection optics unit that detects an image of scattered light originating from the sample irradiated with the illumination light by the illumination optics unit; and an image-processing unit that detects a defect on the sample by processing a signal obtained from the image of the scattered light that the detection optics unit has detected. The detection optics unit includes a plurality of detection optical systems arranged so that oval shaped lenses in which elevation angles of the optical axes thereof are different from each other are arranged within one plane perpendicular to a plane formed by the normal to the surface of the table unit on which to mount the sample and the longitudinal direction of the linear region irradiated with the irradiation light by the illumination optics unit. The detection optical systems each include an objective lens that is the oval shaped lenses formed of circular lenses having left and right portions thereof cut.

In accordance with the present invention, adoption of the configuration outlined above enables high-NA (numerical aperture) detection of images from a plurality of directions, and hence, realization of highly sensitive inspection by effective detection of the light scattered from a microscopic defect.

DESCRIPTION OF THE PREFERRED EMBODIMENTS

Hereunder, embodiments of the present invention will be described using the accompanying drawings.

While the following description takes defect inspection of a semiconductor wafer as an example, the present invention is not limited to the example and can be applied to a method and device for inspecting other objects on which patterns are formed. For example, the invention can also be applied to inspection of substrates used for flat-panel displays such as a liquid-crystal display, plasma display, and organic EL display, and for patterned data-storage products such as discrete track media (DTM) and bit-patterned media (BPM).

First Embodiment

Figure 1:
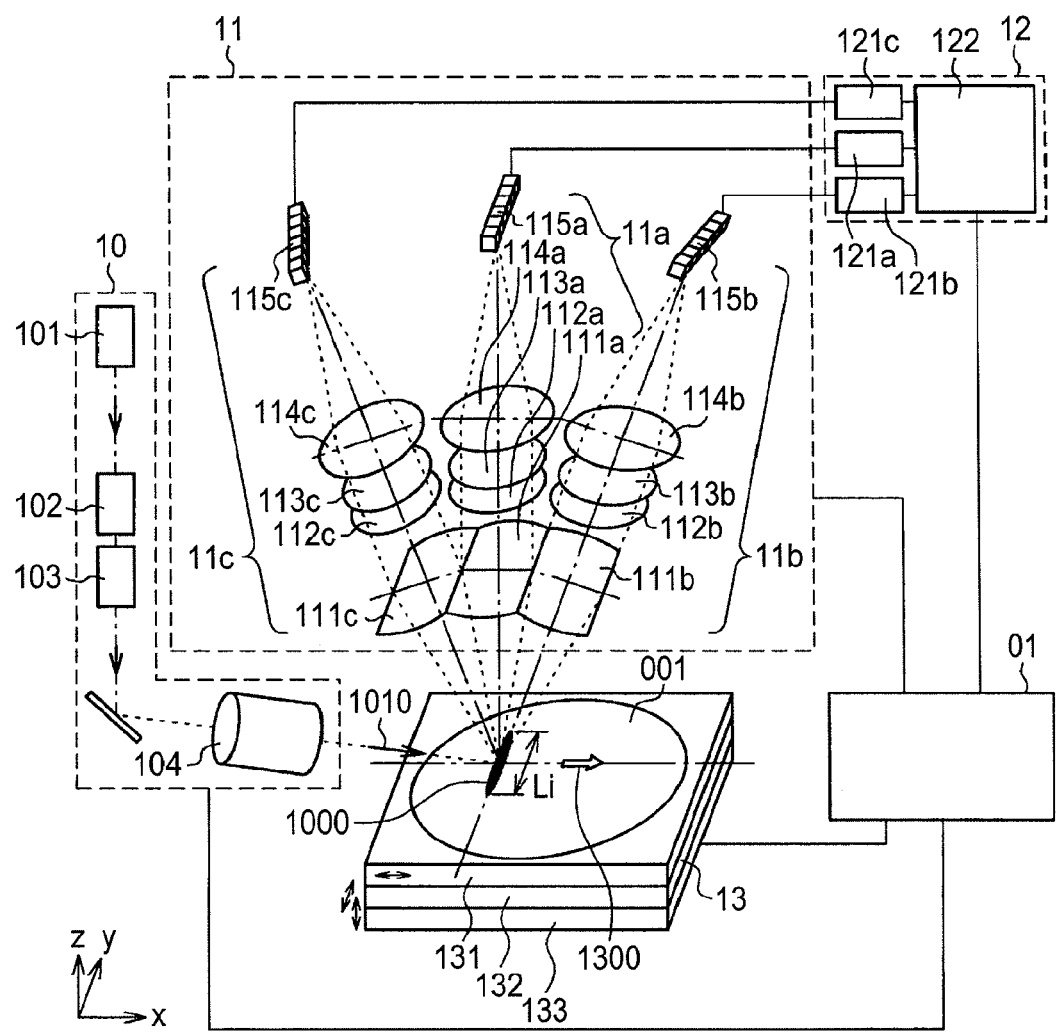
FIG. 1 is a block diagram showing a basic configuration of a defect inspection device in a first embodiment of the present invention.
Figure 2:
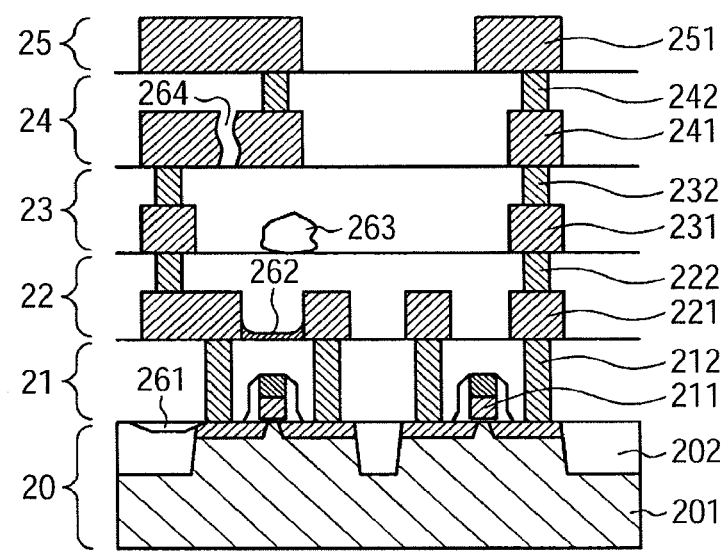
FIG. 2 is a partial sectional view of a patterned substrate to be inspected, the sectional view showing a vertical structure of the patterned substrate and the kinds of defects to be detected.
Figure 3:
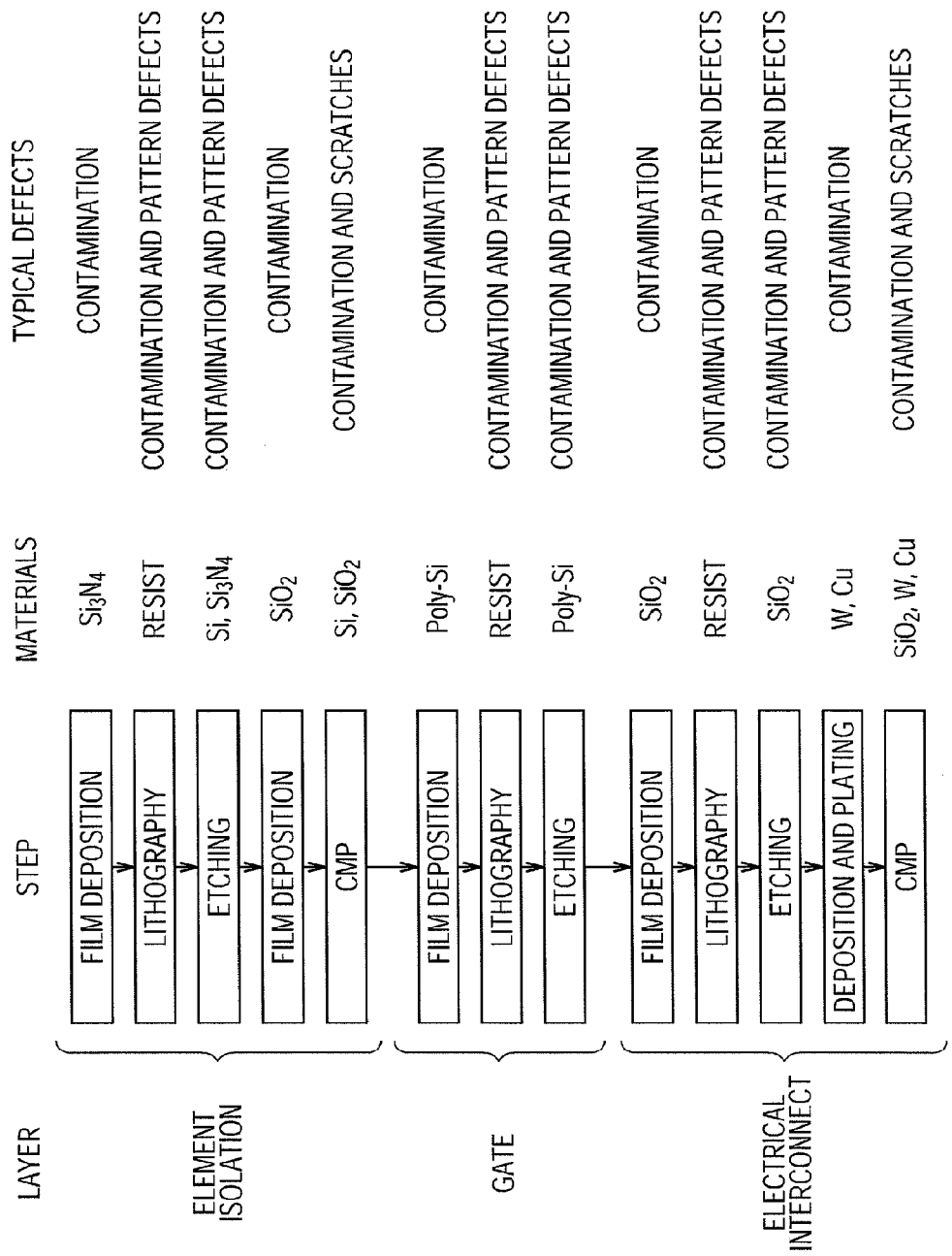
FIG. 3 is a diagram showing a flow of the steps of forming various layers of a semiconductor device, the flow diagram also listing names of materials and typical defects on a layer-by-layer basis.

FIG. 1 shows an example of a defect inspection device configuration as a first embodiment. The defect inspection device according to the present embodiment includes an illumination optics unit 10, a detection optics unit 11, a data-processing unit 12, a stage unit 13, and a total control unit 01.

The illumination optics unit 10 includes a light source 101, a polarization state controller 102, a beam-forming unit 103, and a thin-line converging optics system 104. Illumination light that has emitted from the light source 101 in this configuration is passed through the polarization state controller 102 and the beam-forming unit 103, and then introduced into the thin-line converging optics system 104. The polarization state controller 102 is a member including such polarizers as a half-wave plate and a quarter-wave plate. The polarization state controller 102, further fitted with a driving element (not shown) that is adapted to rotate about an optical axis of the illumination optical system, controls a polarization state of the light used to illuminate a wafer 001 mounted on the stage unit 13. The beam-forming unit 103 is an optical unit that forms thin-line illumination described later herein, and the optical unit includes a beam expander, an anamorphic prism, and the like.

The thin-line converging optics system 104, which includes a cylindrical lens as its major element, illuminates a thin linear illumination region 1000 of the wafer (substrate) 001 with illumination light formed into a shape of a thin line. The description of the present embodiment assumes that as shown in FIG. 1, a cross direction of the thin-line illumination (i.e., a direction perpendicular to a longitudinal direction of the thin-line illumination region) is a stage scan direction 1300 (x-direction) and the longitudinal direction of the thin-line illumination is a y-direction.

In addition, in the present embodiment a narrow region is illuminated in this way by the thin-line illumination, one of purposes of which is to improve inspection throughput by enhancing intensity of the illumination (energy density of the illumination) for the object, that is, the wafer (substrate). To this end, the light source 101 is desirably a laser light source, or a highly converging and highly coherent light source that emits linearly polarized light. Additionally, as discussed in the "Background" hereof, reduction in a wavelength of the light source is effective partly for increasing the amount of light scattered from a defect, and the present embodiment envisages an ultraviolet (UV) laser as the light source 101. For example, the embodiment uses either a YAG (Yttrium Aluminum Garnet)-THG (third-harmonic generation) solid-state laser of 355 nm in wavelength, a YAG-FHG (fourth-harmonic generation) solid-state laser of 266 nm in wavelength, or a 213-nm, 199-nm, 193-nm solid-state laser of a sum-frequency generation type based on a combination of YAG-FHG and YAG fundamental waves.

The light diffracted/scattered from the wafer 001 which has undergone the thin-line illumination from the illumination optics unit 10 is detected through the detection optics system 11. The detection optics system 11 includes three detection units, namely, 11a, 11b, and 11c. Although the configuration with the three detection units is shown in the present embodiment, the detection optics system is not limited to the example and may use two detection units or at least four detection units. Hereinafter, for ease of distinction, constituent elements of the detection unit 11a as a first detection unit, those of the detection unit 11b as a second detection unit, and those of the detection unit 11c as a third detection unit, are expressed with suffixes "a", "b", and "c", respectively, at ends of reference numbers.

The first detection unit 11a includes an objective lens 111a, a spatial filter 112a, a polarizing filter 113a, an imaging lens 114a, and an image sensor 115a. The second detection unit 11b and the third detection unit 11c also include substantially the same optical elements as the above.

Operation of the first detection unit 11a is described below. The diffracted/scattered light from the wafer 001 is converged by the objective lens 111a, and an image of the wafer-scattered light is formed on the image sensor 115a by the imaging lens 114a. The second detection unit 11b and the third detection unit 11c also operate in substantially the same form as the above. That is to say, the diffracted/scattered light is converged by objective lenses 111b, 111c, and images of the wafer-scattered light are formed on image sensors 115b, 115c by imaging lenses 114b, 114c. The objective lenses 111a, 111b, 111c here are each formed by, as shown in FIG. 1, a lens obtained by cutting off left and right end portions of a circular lens rectilinearly (hereinafter referred to as an oval shaped lens). Configurations and advantageous effects of the objective lenses will be described in detail later herein.

The spatial filters 112a, 112b, 112c in the detection optics system 11 block the light regularly diffracted from cyclic patterns regularly formed on the substrate, thereby reduce detection-associated background noise, and improve defect detection sensitivity. The polarizing filters (polarizers) 113a, 113b, 113c are used to filter out a specific polarization component included in detected light, thus reduce background noise, and improve defect detection sensitivity.

The image sensors 115a, 115b, 115c each convert a detected optical image into an electrical signal by photoelectric conversion. In general, charge-coupled device (CCD) sensors, complementary metal-oxide semiconductor (CMOS) sensors, time delay integration (TDI) sensors, or other array sensors are used as the image sensors. Photodiode (PD) arrays, avalanche photodiode (APD) arrays, or photomultiplier tube (PMT) arrays may be used as alternatives to the image sensors.

The above-mentioned thin linear illumination region 1000 on the substrate is illuminated so as to scatter the illumination light collectively toward a detection range of the image sensor 115 for enhanced illumination efficiency (this avoids inefficient illumination that causes scattering in a direction overstepping the detection range of the image sensor). The present embodiment assumes that the image sensors 115a, 115b, 115c are line sensors.

The three detection units, 11a, 11h, 11c, arranged in the detection optics system 11 of the present embodiment are of the same construction. This reduces any differences in quality between the scattered-light images detected by the detection units, and thereby raises extraction accuracy of a defect signal, based on comparison results of the scattered-light images obtained by the different detection units during imaging. The arrangement of the detection units having the same construction also helps reduce a manufacturing man-hour requirement and manufacturing cost of the inspection device.

The data-processing unit 12 uses signal-processing units 121a, 121b, 121c to conduct A-D conversion of the detection image signals which the first, second, and third image sensors, 115a, 115b, 115c, have acquired by photo-electric conversion, and then to generate inspection image data by conducting a process such as noise reduction or noise removal.

Reference number 122 denotes an image-processing unit, in which the inspection image data that the signal-processing units 121a, 121b, 121c have generated undergoes image processing based on comparison with reference image data and a defect signal is extracted from comparison results. The reference image data may be created from design data relating to the circuit patterns formed on the wafer, or may be stored image data obtained after imaging of those patterns on different sections of the wafer that originally have the same shape as that of any one of the patterns, or may be image data obtained between different detection units by imaging the same section on the wafer.

In the extraction of the defect signal, information contained in the scattered-light images which have been obtained by the first, second, and third detection systems (optics) undergoes processing and the defect is extracted. During the extraction of the defect signal, not only the image obtained by each detection system is subjected to independent processing, the images obtained by the different detection systems are also subjected to comparative processing.

The control unit 01 controls the illumination optics system 10, the detection optics system 11, the data-processing unit 12, and the stage unit 13.

The stage unit 13, which is a mechanism that moves the mounted wafer 001 in xyz directions, includes an X-stage 131 and a Y-stage 132, each of which has an x-axial or y-axial movement stroke to enable the detection optics system 11 to inspect the entire wafer surface, and a Z-stage 133 has a z-axial movement stroke to control a z-position of the wafer surface (the surface to be inspected) within a focus range of the detection optics system 11, even if the wafer is not uniform in thickness.

Stage movements of the stage unit 13 during inspection are controlled in the following fashion. As shown in FIG. 1, the wafer 001 is illuminated at the thin linear illumination region 1000 having a longitudinal dimension as length "Li" in a direction of the y-axis. During inspection, the X-stage 131 continuously moves the wafer 001 in a direction 1300 of the x-axis and the three detection units of the detection optics system 11 scan the wafer to acquire images.

In the example of FIG. 1, where, for example, a left edge of the wafer is taken as a starting position of movement, the X-stage 131 moves the wafer until the stage has reached an opposite edge (right edge) of the wafer, and the detection optics system 11 scans across the wafer surface, that is, between the left and right edges. After the opposite (right) edge of the wafer has been reached, in order to provide for next scan, the Y-stage 132 moves the wafer in steps through the length "Li" of the illumination region 1000 in the direction of the y-axis, then the X-stage 131 continuously moves in a direction opposite to that of the previous movement, and the detection optics system 11 acquires wafer images by scanning the wafer in substantially the same manner as that of the previous scan. The entire wafer surface is inspected by repetition of such processing.

During scanning, if the wafer goes out of the focus range of the detection optics system 11, the quality of the wafer images acquired will deteriorate and defect detection sensitivity will decrease. In order to avoid this, the z-position of the wafer surface is controlled by the Z-stage 133 to always stay within the focus range of the detection optics systems 11 during scanning. The z-position of the wafer surface is detected by a wafer surface z-position detection device not shown.

Defocusing significantly affects the quality of the acquired wafer images and can be a cause of a significant decrease in defect detection sensitivity. In order to avoid this, the illumination optical system and the detection optical system are constructed as follows in the present embodiment: the detection units having the same construction in the detection optics system are arranged so that respective optical axes differ from one another in detection angle of elevation in one plane (hereinafter, this plane is referred to as the detection optical-axis plane) and so that the detection optical-axis plane is perpendicular to a plane formed by two elements, that is, a line normal to the object surface to be inspected, and the longitudinal direction of the thin linear illumination region 1000.

Since the detection units are arranged in this form, when the same detection optics system is disposed in plurality and scattered light is detected from different directions, distances from those points within a detection range, on the surface to be inspected, that are detected by the image sensors (line sensors) of the detection optics system 11, to detection surfaces of the image sensors, can be kept the same and even without a special mechanism, scattered-light images in focus can be obtained over entire detection regions of the image sensors (line sensors).

The objective lenses 111a, 111b, 111c of the present embodiment, described earlier, are each formed using an oval shaped lens of a left-right symmetrical shape that is obtained by cutting off the left and right end portions of a circular lens rectilinearly, and are arranged so that the cut rectilinear portions are perpendicular to the detection optical-axis plane described above. When a plurality of detection units are arranged, therefore, the use of the oval shaped lenses, compared with the use of ordinary circular lenses, enables the extension of a detection aperture for enhanced capturing efficiency of the scattered light. The use of the oval shaped lenses also enables the acquisition of in-focus scattered-light images over the entire detection regions of the image sensors (line sensors) 115a, 115b, 115c. The use of the oval shaped lenses additionally enables the detection of uniform image quality over the entire detection regions of the image sensors (line sensors) by constructing symmetrical optics with respect to the plane formed by the longitudinal direction of the image sensors (line sensors) 115a, 115b, 115c and the optical axes of the detection units 11a, 11b, 11c.

In addition, the plurality of detection units (in the present embodiment, three units, namely 11a, 11b, 11c) are arranged so that the respective optical axes are symmetrical with respect to the plane formed by two elements, that is, the line normal to the object surface to be inspected, and the longitudinal direction of the thin linear illumination region 1000 on the object surface. When the images acquired by different sets of detection optics systems undergo comparative processing for the extraction of a defect signal, the above arrangement of the detection units facilitates comparative processing of those images. For example, detecting one position from the left and right sides thereof at the same detection angle of elevation in the above arrangement enables the acquisition of two scattered-light images having substantially the same quality and reflecting only the difference in the direction of occurrence of the scattered light, and then executing comparative processing of the two images enables highly accurate extraction of a defect signal. Furthermore, at least one of the plurality of detection units (in the present embodiment, three units, namely 11a, 11b, 11c) in the present embodiment is disposed so that the corresponding optical axis is in alignment with the line normal to the object surface to be inspected. This disposition facilitates device state monitoring with reference image quality assigned to the image acquired through the particular detection unit.

As will be described later herein, the detection optical systems for oblique detection (in the present embodiment, the detection units 11b, 11c) are liable to significantly deteriorate the quality of the detection images (scattered-light images) in case of defocusing. In the present embodiment, a plurality of detection units having the same configuration are arranged and if their original performance is exhibited, the scattered-light images acquired by the detection units will have substantially equal quality. At this time, however, if all detection units of the device are constructed only of the oblique-detection optical systems, it is estimated that all the units will cause similar image deterioration due to defocused oblique detection. In addition, if this actually occurs, it will be difficult to determine to what extent the actually acquired image quality satisfies the image quality that originally ought to be obtained.

If one detection unit (in the configuration of FIG. 1, the detection unit 11a) is disposed so that its optical axis is in alignment with the line normal to the object surface to be inspected, the deterioration of a detection image in the corresponding optics due to defocusing will be less significant than that of the other detection units for oblique detection (in the present embodiment, the detection units 11b and 11c). Accordingly, when the quality of the scattered-light image acquired by the particular optics is adopted as a reference, the quality of the scattered-light images acquired by the other units can be appropriately evaluated and device state monitoring and on-trouble adjustment become easy.

A configuration of the oval shaped lenses in the present embodiment is described below using FIGS. 4 to 7.

Figure 4:
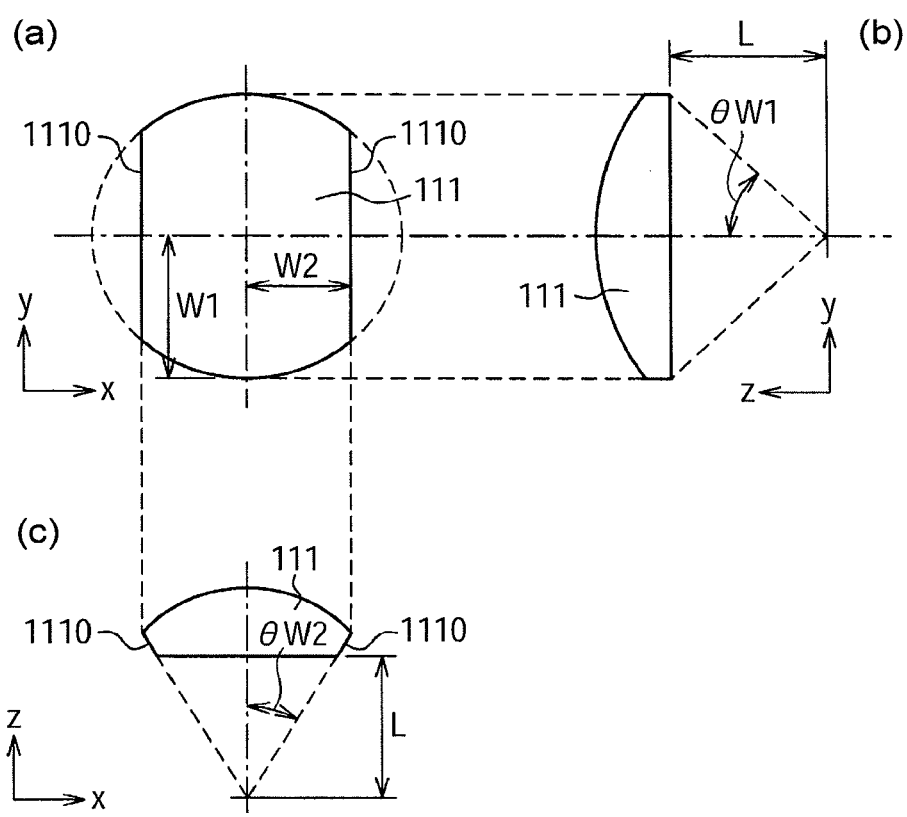
FIG. 4 is a plan view (a), side view (b), and front view (c) of an oval shaped lens used in the first embodiment of the present invention.

FIG. 4 is an explanatory diagram illustrating a single-lens shape of one oval shaped lens, 111. This planar shape of the oval shaped lens 111 is created by, as shown in FIG. 4(a), cutting a circular lens along two rectilinear cutting planes, 1110, thereof into an oval shaped of a left-right symmetrical shape. A side shape is created by, as shown in FIG. 4(c), cutting the lens obliquely so that if a detection aperture angle obtained in a short-side direction of the single lens by combining the lens in plurality to construct a composite lens assembly is expressed as θW2, a distance from a focus plane of each lens as L, and half width of the lens as W2, then a relationship of W2≈L·tan θW2 exists. Thus the x-axial detection aperture θW2 of the lens, shown in FIG. 4(c), differs from a y-axial aperture θW1 shown in FIG. 4(b), and it follows that θW1>θW2. The following describes how the oval shaped lenses are to be arranged in the actual device to realize such a relationship.

Figure 5:
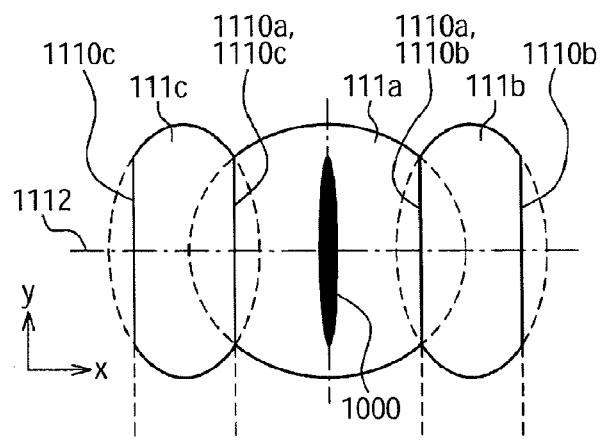
FIG. 5 is a plan view (a) and front view (b) of oval shaped lenses as arranged in the first embodiment of the present invention.

FIG. 5 is a diagram that illustrates layout of the oval shaped lenses in the inspection device. Section (a) of FIG. 5 is a plan view of the oval shaped lenses, and section (b) is a front view thereof. The three oval shaped objective lenses, 111a, 111b, 111c, in an x-y plane of FIG. 5(a) all have the same aperture, but since the optical axes of the objective lenses 111b, 111c are inclined and these two objective lenses are shown in x-y plane view, the two objective lenses are depicted as if both were seemingly smaller than the objective lens 111a.

The three oval shaped objective lenses, 111a, 111b, 111c, are arranged so that respective focus positions match the position of the thin linear illumination region 1000. At this time, the optical axes of the oval shaped objective lenses 111a, 111b, 111c meet together on one such planar section of the detection optical-axis plane 1112 that is perpendicular to the plane formed by two elements, that is, the line 1111 normal to the surface of the wafer 001, and the longitudinal direction (y-axis direction) of the thin linear illumination region 1000. In addition, the optical axes are of symmetrical layout about the line 1111 normal to the surface of the wafer 001. The cutting planes 1110a, 1110b, 1110c of each lens are as close as possible to one another, and are also substantially parallel to one another. Furthermore, the cutting planes 1110a, 1110b, 1110c of the lens are oriented in a direction parallel to the longitudinal direction of the thin linear illumination region 1000, and when inspection images are acquired, the wafer is scanned in a direction 1300 perpendicular to the direction of the cutting planes.

The detection aperture of the lens has the angle of θW2 in the x-direction and the angle of θW1 in the y-direction. While the aperture size of the lens as considered as an independent element is greater in the y-direction than in the x-direction, combination of the lenses 111a, 111b, 111c enables an aperture of the entire composite lens assembly to be extended in the x-direction.

Figure 6:
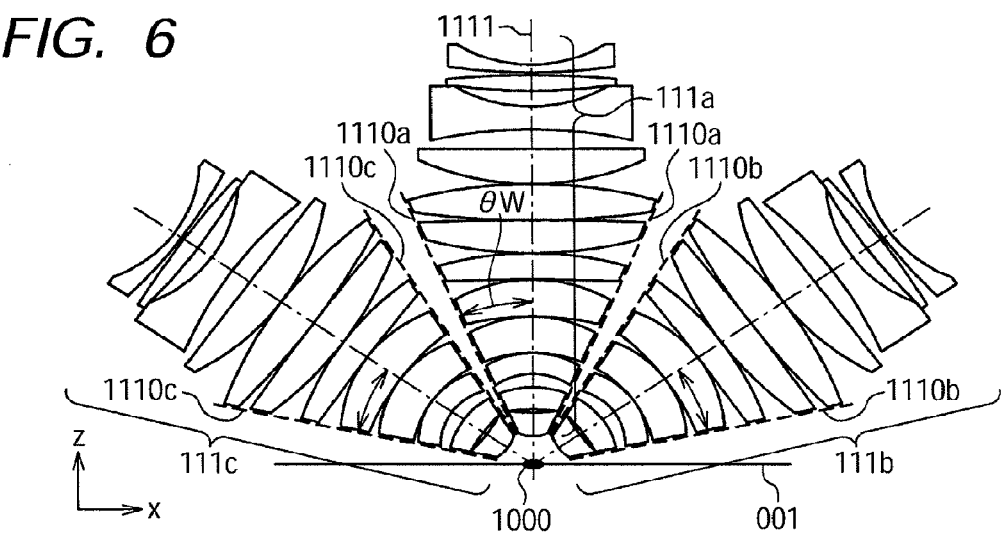
FIG. 6 is a front view of oval shaped lenses that illustrates an example in which the oval shaped lenses in the first embodiment of the present invention are constructed using composite lenses.

FIG. 6, which assumes that the actual objective lenses are composite lens assemblies each formed from a combination of single lenses, is an explanatory diagram illustrating an example in which each of the composite lens assemblies is constituted by oval shaped lenses. FIG. 6 shows an example in which each objective lens assembly 111a, 111h, 111c is constructed using 12 composite lenses. In this case, not all of the 12 lenses need to be oval shape lenses. Since an increase in distance from the wafer 001 also causes an increase in distance between the optical axes of the lenses, if the lenses are circular, interference between them is likely, so these interfering lenses are preferably replaced by oval shaped lenses.

In the present embodiment, since interference between circular lenses is likely, nine lenses closer to the wafer are oval shaped lenses. A basic state of cutting is the same as that described in FIG. 4. That is to say, the nine front lenses of each of the objective lens assemblies 111a, 111b, 111c are formed from circular lenses cut for a detection aperture angle θW, along cutting planes 1110a, 1110b, 1110c.

The three rear lenses, which do not interfere with each other, need no cutting, so they are not cut. In addition, as in FIG. 5, the three objective lenses, 111a, 111b, 111c, are arranged so that respective focus positions match the position of the thin linear illumination region 1000. At this time, the optical axes of the oval shaped objective lenses 111a, 111b, 111c meet together on one plane (equivalent to the detection optical-axis plane 1112) that is perpendicular to the plane formed by two elements, that is, the line 1111 normal to the surface of the wafer 001, and the longitudinal direction (y-axis direction, not shown) of the thin linear illumination region 1000. In addition, the optical axes are of symmetrical layout about the line 1111 normal to the surface of the wafer 001. The cutting planes 1110a, 1110b, 1110c of each lens are as close as possible to one another, and are also substantially parallel to one another.

Figure 7:
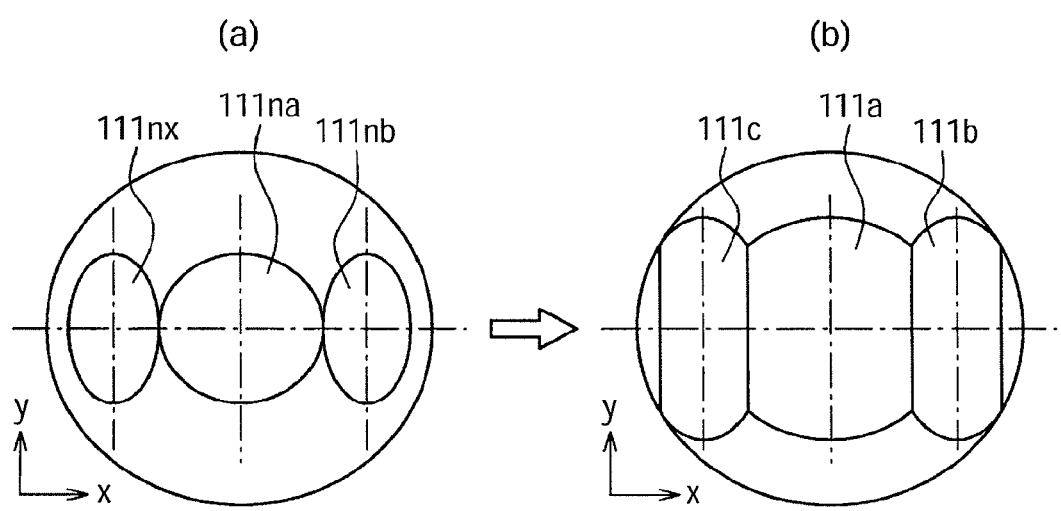
FIG. 7 is a plan view (a) showing an example in which various objective lenses of detection units are each composed of a circular lens, and a plan view (b) showing an example in which the objective lenses are each composed of an oval shaped lens.

FIG. 7 is an explanatory diagram that illustrates advantages arising from adopting oval shaped lenses. FIG. 7(a) shows apertures obtained when light is detected from three different directions using circular lenses 111na, 111nb, 111nc of the same size. The apertures of the lenses are all of the same size and circular, but since the optical axes of the objective lenses 111nb, 111nc are inclined and these two objective lenses are shown in x-y plane view, the two objective lenses are depicted as if both were seemingly smaller than the objective lens 111na.

To avoid lens-to-lens interference in this case, it is necessary to make the lens apertures, and since these apertures are circular, it is further necessary to make the apertures smaller in both an x-direction and a y-direction. The detection optics system in the present example assumes forming wafer images with the imaging optics, and for this purpose, envisages a condition of arranging the plurality of objective lenses so that the respective optical axes meet together in one plane. For this reason, if a plurality of circular lenses are arranged on the above assumption, this arrangement is likely to cause an inconvenience of the detection aperture sizes being very much limited, especially the y-axial dimension of each detection aperture becoming too small.

On the other hand, if as shown in FIG. 7(b), oval shaped objective lenses 111a, 111b, 111c are adopted and x-axial and y-axial aperture dimensions of each of the objective lenses are made to be optionally settable, it suffices just to make the x-axial aperture of one objective lens smaller for avoidance of interference and arrange a correspondingly larger number of lenses in the x-direction. Additionally, any necessary y-axial aperture dimensions of the lenses can be set, irrespective of the x-axial aperture dimension(s), and even if an image is to be detected using a plurality of sets of detection optics systems, capturing efficiency of scattered light can be significantly improved in comparison with a case in which the detection optics system is constituted by circular lenses.

Figure 8:
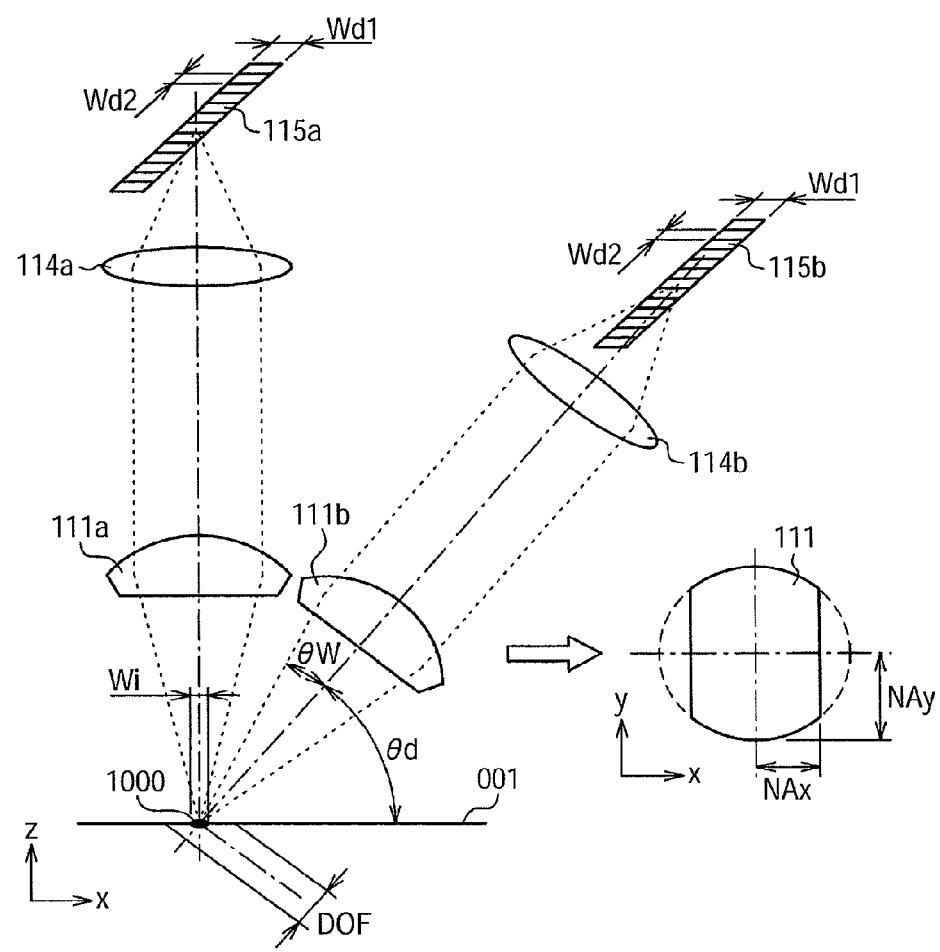
FIG. 8 is a block diagram of a detection optical system that illustrates thin-line illumination as used in the first embodiment of the present invention.

Next, necessity for the thin-line illumination in the present embodiment is described below using FIG. 8. In addition to objective lenses 111a and 111b, a third objective lens is actually located to the left of the objective lens 111a, and thus three detection units constitute a detection optics system. For simplicity, however, the detection unit actually present at the left of the objective lens 111a is omitted and an example assuming that the detection optics system is constituted by two detection units is described here.

This example assumes that a second detection unit shown with suffix "b" has an optical axis inclined at an elevation angle $\theta d$ with respect to the surface of the wafer 001 that is to be inspected, and that the objective lens 111b has an aperture angle $\theta W$, that is, the objective lens 111b has an x-axial numerical aperture NAx represented as follows:

$$NAx = \sin \theta W \quad \text{(Numerical expression 1)}$$

When the wavelength of the illumination light source is expressed as $\lambda$, if a depth of focus of the objective lens 111b is expressed as DOF, then:

$$DOF = \lambda/(\sin \theta W)^2 \quad \text{(Numerical expression 2)}$$

The thin linear illumination region 1000 on the wafer is illuminated with an illumination width "Wi" of light. If the illumination light oversteps a DOF range of the objective lens 111b of the second detection unit, scattered light from regions outside the DOF range will enter and images of the scattered light will contain a blurring component, which will in turn deteriorate the image quality of the scattered light, thus reducing defect detection sensitivity. To prevent the reduction in sensitivity from occurring, it is necessary that the thin linear illumination region 1000 and the illumination width "Wi" should fall within the DOF range of the objective lens 111b of the second detection unit, that is, that the following relationship should hold:

$$Wi < DOF/\sin \theta d \quad \text{(Numerical expression 3)}$$

In addition to this, depending on control accuracy of the z-stage, the detection position of the wafer is likely to move in the direction of the optical axis of the second detection optical unit. If the control accuracy of the z-stage is taken as $\pm \Delta z$, the change in the detection position can be expressed as follows:

$$\pm \Delta z/\cos \theta d \quad \text{(Numerical expression 4)}$$

Putting these together, the following becomes the condition necessary to acquire blur-free images of scattered light in the oblique-detection optical systems:

$$DOF/\sin \theta d > Wi + 2 \times (\Delta z/\cos \theta d) \quad \text{(Numerical expression 5)}$$

When a magnification of the second detection optical unit is expressed as M, the image sensor (line sensor) 115b in the oblique-detection optical system 12 desirably has the following value as a pixel size Wd1 in the scanning direction of the x-stage:

$$Wd1 \geq M \times Wi \times \sin \theta d \quad \text{(Numerical expression 6)}$$

This is because the image sensor 115b needs to detect the scattered light originating from all illumination regions, improve detection efficiency of the scattered light, and hence improve inspection throughput. In other words, if the pixel size Wd1 of the image sensor 115b is such that $$Wd1 < M \times Wi \times \sin \theta d \quad \text{(Numerical expression 7)}$$

and the detection range is limited to a portion of the illumination range, then the illumination light falling outside the detection range of the image sensor 115b will not be used effectively, the amount of light detected will decrease, and inspection throughput will also decrease.

Similarly, the image sensor 115a of a first detection unit shown with suffix "a" desirably satisfies the following relationship in terms of illumination light utilization efficiency:

$$Wd1 \leq M \times Wi \quad \text{(Numerical expression 8)}$$

For reduced device costs, the inspection device of the present embodiment assumes that the respective objective lenses 111a, 111b, imaging lenses 114a, 114b, and image sensors 115a, 115b of the first and second optical units for detection are common in specifications. Depending on the device configuration, therefore, the larger of the values predetermined per numerical expressions 6 and 8 can be set as a pixel size Ws1 of the image sensors 115a, 115b in the scanning direction of the stage.

A pixel size Wd2 of the image sensors 115a, 115b, in a direction (y-direction, sensor arrayal direction) perpendicular to the scanning direction of the stage, does not need to be the same as Wd1. Signals are desirably sampled at a rate N (N=1, 2 . . . ) based on y-axial resolution of the objective lenses 111a, 111b, that is, on numerical expression 9 defined from the formula relating to the Rayleigh's diffraction limit. Briefly, a preferable value of the pixel size is:

$$Wd2 = (0.61 \times \lambda/NAy)/N (N=1,2 \ldots) \quad \text{(Numerical expression 9)}$$

An appropriate sampling rate N to be assigned subject to the Nyquist theorem is at least 2, and if possible, nearly 4. However, even if a larger value is assigned (i.e., even if the pixel size is made smaller than necessary), this is ineffective in terms of the improvement of inspection image quality and only results in narrowed inspection area and hence in reduced inspection throughput, so that the appropriate value within the above range needs to be set.

For these reasons, the pixels of the image sensors in the present embodiment are desirably the rectangular pixels that satisfy Wd1>Wd2, that is, the pixels whose size generally differs between the scanning direction of the stage and the direction perpendicular to this scanning direction.

In the present embodiment, which envisages the use of the oval shaped lenses, whereas the x-axial lens numerical aperture NAx is restricted by the arrangement of the lenses, the y-axial lens numerical aperture NAy is not subject to the restriction. Increasing NAy without any such restriction, therefore, enables Y-axial resolution to be raised and thus the image quality of the scattered light to be correspondingly enhanced. X-axial resolution can likewise be raised, regardless of the aperture sizes of the lenses, by reducing the line width "Wi" of the thin-line illumination below the x-axial lens resolution of $0.61 \times \lambda/NAx$ and narrowing the illumination range. The use of the oval shaped lenses is particularly effective in a case that the number of detection units is increased and the x-axial aperture sizes of the objective lenses are correspondingly reduced.

An example in which the three detection units, 11a to 11c, of the detection optics system 11 all include the same optical elements has been described in the above embodiment. However, the present invention is not limited to this configuration and may adopt a configuration in which the objective lens 111a of the first detection unit 11a is made larger than the objective lenses 111b and 111c of the second and third detection units 11b and 11c. Thus, the light scattered perpendicularly relative to the wafer 001 and the light scattered in a vicinity thereof will be converged in greater amounts by that objective lens 111a to form the images obtained. With this configuration, the detection optics system can have the NA of the first detection unit 11a increased and detect even more microscopic defects with the first detection unit 11a.

Second Embodiment

Changes in ambient environment significantly affect the image quality of the scattered light. Although changes in temperature can be accommodated by merely providing a temperature control mechanism inside the device, it is difficult in terms of costs to provide, against changes in atmospheric pressure, a structure or mechanism that keeps an internal atmospheric pressure of the entire device constant.

Figure 9A:
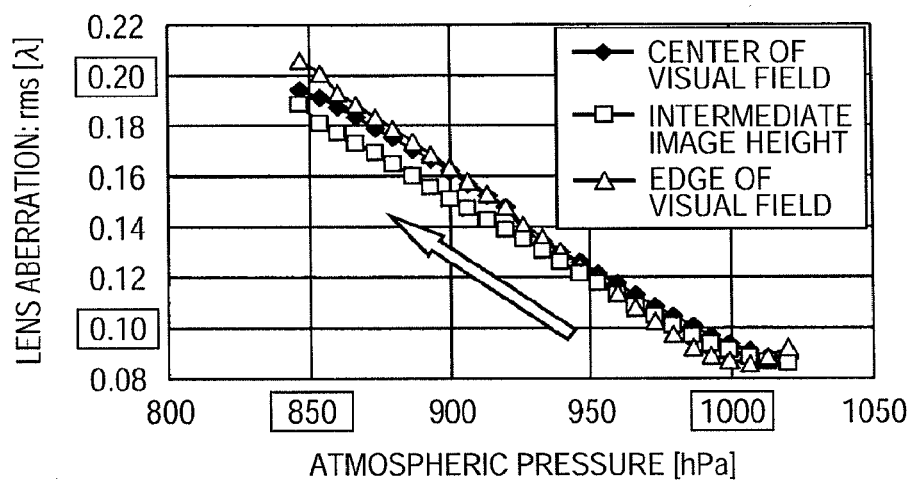
FIG. 9A is a graph representing a relationship between atmospheric pressure and lens aberration.
Figure 9B:
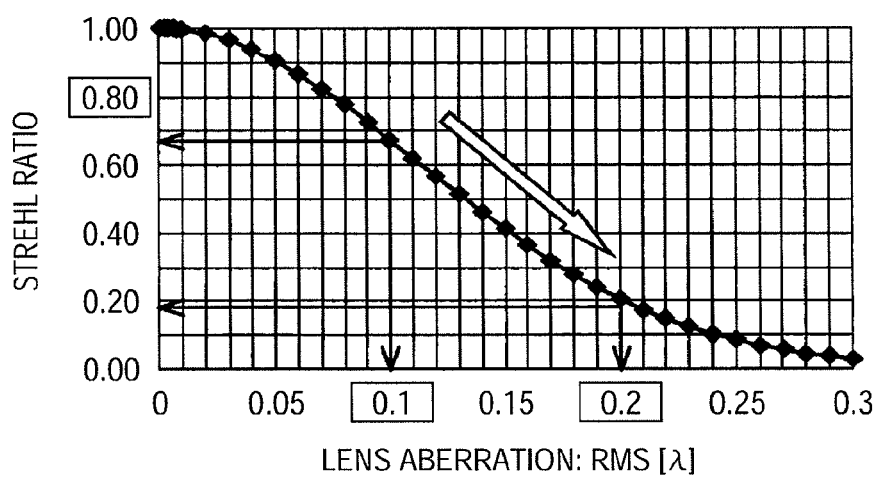
FIG. 9B is a graph representing a relationship between lens aberration and Strehl ratio.

FIGS. 9A and 9B are diagrams that explain impacts of atmospheric pressure changes upon the deterioration of image quality. FIG. 9A shows calculation results that indicate how changes in atmospheric pressure vary lens aberration. For example, even if a lens is assembled and adjusted under an environment of 1,000 hPa and aberration is controlled below $0.1\lambda$, a decrease of the atmospheric pressure to 850 hPa degrades aberration to $0.2\lambda$.

The degradation in aberration is a component that cannot be sufficiently corrected by adjustment of the imaging position, as in the prior-art devices discussed earlier herein. FIG. 9B illustrates the adverse effects of such degradation upon images of scattered light. In the case that aberration degrades from $0.1\lambda$ to $0.2\lambda$, the Strehl ratio that represents theoretical point-imaging performance decreases below ⅓ of its original value. This means that a blur of the image degrades by a factor of three. If such image deterioration occurs, defect detection performance that has been obtained under the original environment of 1,000 hPa in atmospheric pressure cannot likewise be achieved under the environment of 850 hPa in atmospheric pressure.

In the present embodiment, therefore, a function that prevents image quality from deteriorating even if a change in atmospheric pressure occurs during inspection is imparted to the defect inspection device described in the first embodiment.

Figure 10:
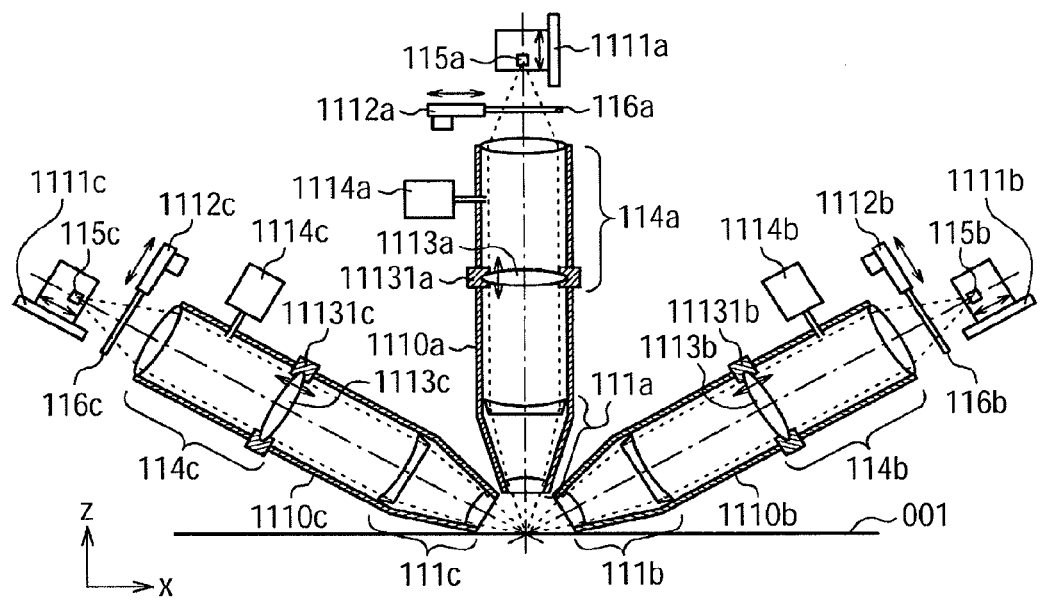
FIG. 10 is a front view showing schematically a detection optical system configuration including a mechanism to correct a change in ambient air pressure in a second embodiment of the present invention.
Figure 11:
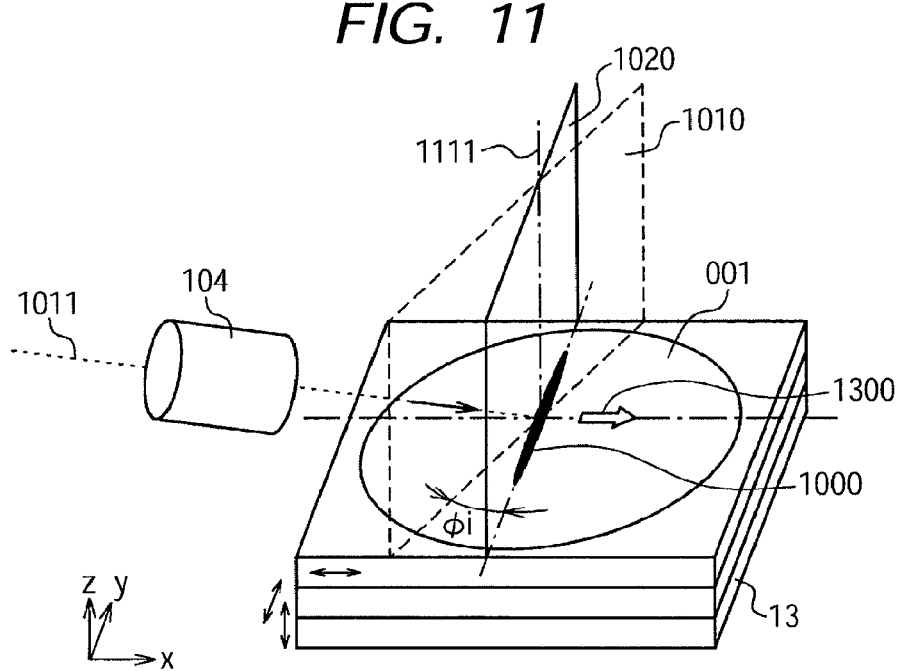
FIG. 11 is a perspective view of a patterned substrate as mounted on a stage unit prior to defect inspection, the perspective view illustrating a direction of illumination by an illumination optical system in the second embodiment of the present invention.

FIGS. 10 and 11 are diagrams that explain mechanisms assigned to lenses to correct the deterioration of image quality. Not all these correction mechanisms need to be provided and it suffices if, among these mechanisms, at least one or more appropriate kinds of mechanisms are added according to mechanism-mounting conditions and in a feasible correction range that does not cause the deterioration of the scattered-light images detected.

The configuration shown in FIG. 10 relates to the optics corresponding to the first detection unit 11a, second detection unit 11b, and third detection unit 11c of the first embodiment described using FIG. 1. In the present (second) embodiment, constituent elements not shown are the same as those described in the first embodiment, and description of these elements is therefore omitted hereinafter.

Referring to FIG. 10, elements 1111a, 1111b, 1111c for moving image sensors in directions of optical axes are mechanisms that move the image sensors in directions of arrows, that is, directions along optical axes of imaging lenses 114a, 114b, 114c, in response to changes in imaging positions of the lenses due to changes in ambient air pressure. Mechanisms 1112a, 1112b, 1112c provide aberration correction by inserting/removing parallel flat plates. A change in performance of a lens, associated with a change in ambient air pressure, is due to a change in the refractive index of air, caused by the change in ambient air pressure. In order to compensate for a decrease in the refractive index of air due to a decrease in atmospheric pressure, the parallel flat plates, which are high-refractive-index media, are inserted into/removed from optical paths of the imaging lenses 114a, 114b, 114c, to correct aberration.

Lens actuators 11131a, 11131b, and 11131c each move one lens 1113a, 1113b, or 1113c within lens groups constituting the imaging lenses 114a, 114b, 114c, in a direction of an arrow, that is, the direction along the optical axis of the imaging lens 114a, 114b, 114c. Controlling a position of the lens 1113a, 1113b, 1113c via the corresponding lens actuator 11131a, 11131b, and 11131c enables performance of the imaging lens 114a, 114b, 114c to be corrected and thus a change in the performance of the lens due to a change in atmospheric pressure to be compensated. Air pressure controllers 1114a, 1114b, 1114c control internal air pressures of lens tubes 1110a, 1110b, 1110c by keeping the inside of each lens tube 1110a, 1110b, 1110c airtight, thereby to maintain constant lens performance. With the air pressure controllers, internal environments of the lens tubes 1110a, 1110b, 1110c can be blocked from their external environments to maintain the internal air pressures of the lens tubes 1110a, 1110b, 1110c at the same level as during lens assembly and adjustment, and hence to maintain constant lens performance even under changing air pressures.

FIG. 10 shows an example in which the detection units are provided with a mechanism that corrects a change in lens performance due to a change in atmospheric pressure. This correction mechanism can also be provided in illumination optics systems. An example of illumination optics systems provided with the correction mechanism is described below using FIG. 11.

The reason why the change in lens performance due to a change in atmospheric pressure occurs is that the change in atmospheric pressure causes a change in the refractive index of air, a medium that fills in a space between lenses. When atmospheric pressure decreases, the density of air also decreases, which in turn reduces the refractive index of air.

A beam of light that passes through lenses is bent according to particular differences between refractive indexes of the lens materials (glass, quartz, or others) and the refractive index of air, the medium lying between the lenses. Thus, scattered light that has originated from the wafer propagates through the lenses and forms an image on an image sensor. If the ambient air pressure changes and thus the refractive index of air changes, an extent to which the beam of light that passes through the lenses is bent will also change and a state of the image formed on the image sensor will change as a result. Normal lens design is based on a prerequisite of 1 atmosphere (1,013 hPa) in ambient air pressure, and lenses are designed to develop best imaging performance under that environment. Imaging performance deteriorates for atmospheric pressure variations departing from the prerequisite.

The refractive indexes of the materials, on the other hand, differ according to a wavelength of the light passing through them. Utilizing this relationship allows a decrease in the imaging performance of the lenses due to a change in atmospheric pressure to be corrected by varying the wavelength of the light passing through the lenses, that is, the wavelength of the illumination light source.

Figure 13:
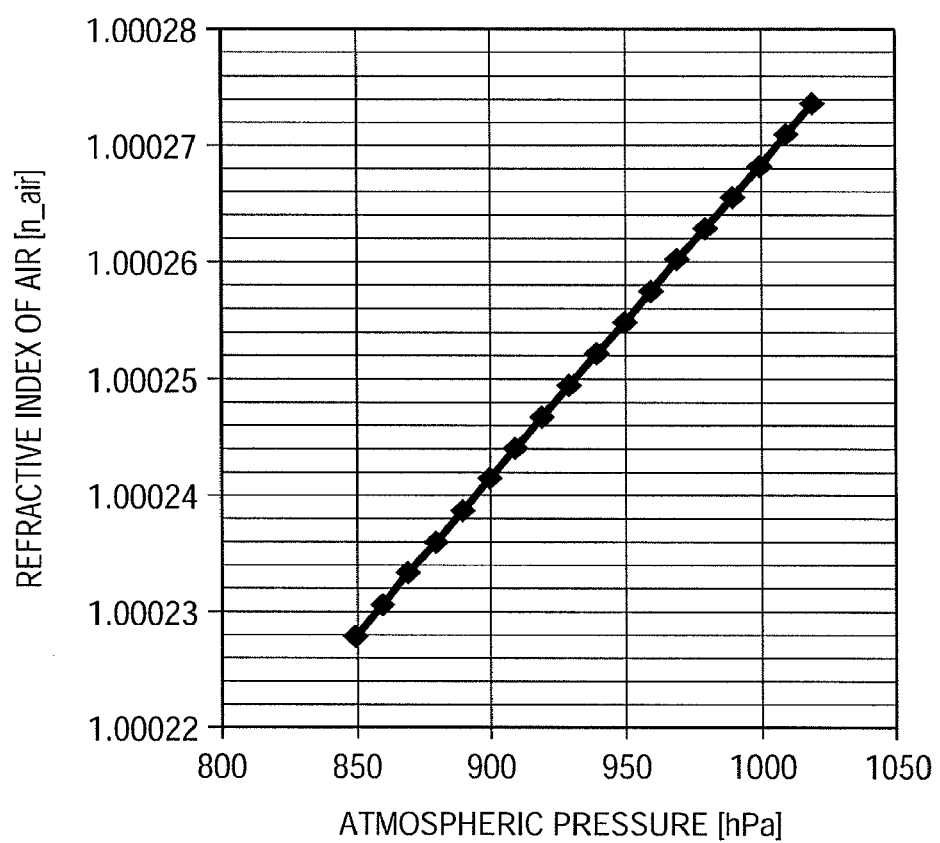
FIG. 13 is a graph of changes in refractive index of air, plotted against changes in atmospheric pressure.

FIG. 13 is a graph that indicates changes in the refractive index of air, plotted against changes in atmospheric pressure. According to Non-Patent Document 2, the relationship between the refractive index of air, $n_{air}$, air temperature T (°

C.), and atmospheric pressure (Torr), is represented by numerical expression (10) as follows:

$$n_{air}=1+(3.83639\times10-7\times P)(1+P(0.817-0.0133T)\times10-6)/(1+0.03661T)$$ (Numerical expression 10)

FIG. 13 is a graph based on numerical expression 10, representing how the refractive index of air ($-n_{air}$) will vary as atmospheric pressure changes from 850 to 1,020 [hPa]. The variation in the refractive index of air ($n_{air}$) is nearly $4.56\times10^{-5}$ for the change of 170 [hPa] in atmospheric pressure. As can be seen from this fact, when the atmospheric pressure changes, the refractive index also changes. These changes in the refractive index of air ($n_{air}$) cause such changes in lens performance that are shown in FIGS. 9A, 9B.

Figure 14:
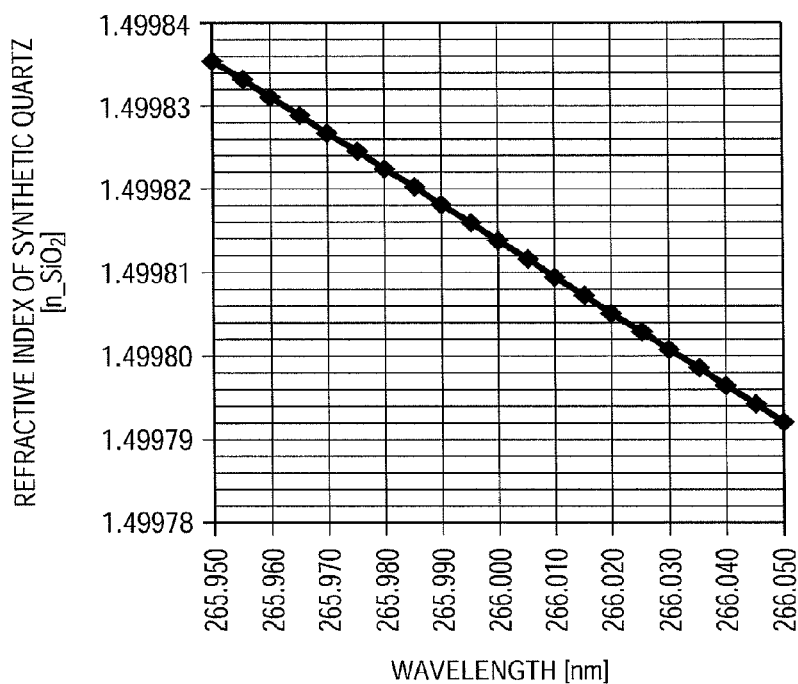
FIG. 14 is a graph of changes in refractive index of synthetic quartz, plotted against changes in wavelength of light passed through a lens.

FIG. 14, on the other hand, is a graph based on the Sellmeier's equation (Non-Patent Document 3), representing changes in refractive index ($n_{siO2}$) of synthetic quartz, a typical lens material, plotted against changes in the wavelength of the light passing through the lens. When the wavelength increases, the refractive index decreases, and when the wavelength increases by 0.1 nm (100 μm) from 265.95 nm to 266.05 nm, the refractive index decreases by nearly $4.33\times10^{-5}$.

Utilizing these relationships makes it possible, when ambient air pressure decreases (the refractive index of air, $n_{air}$, decreases), to control the wavelength of the light source for a shift to a greater wavelength, and thus to keep refractive power of the lens constant, that is, maintain a constant difference in refractive index between air and synthetic quartz $n_{siO2}-n_{air}$), by reducing the refractive index of synthetic quartz ($n_{siO2}$) as well. Thus, even when the ambient air pressure changes, the performance of the lens can be kept substantially equal to its design value based on the prerequisite of 1 atmosphere=1,013 hPa.

Next, mechanisms that change the wavelength of the illumination light source are described below using FIGS. 15 and 16.

As discussed earlier herein, a high-coherence and high-power short-wavelength light source is desirable for the darkfield type of defect inspection device. Mechanisms based on this are also described in the examples below.

Figure 15:
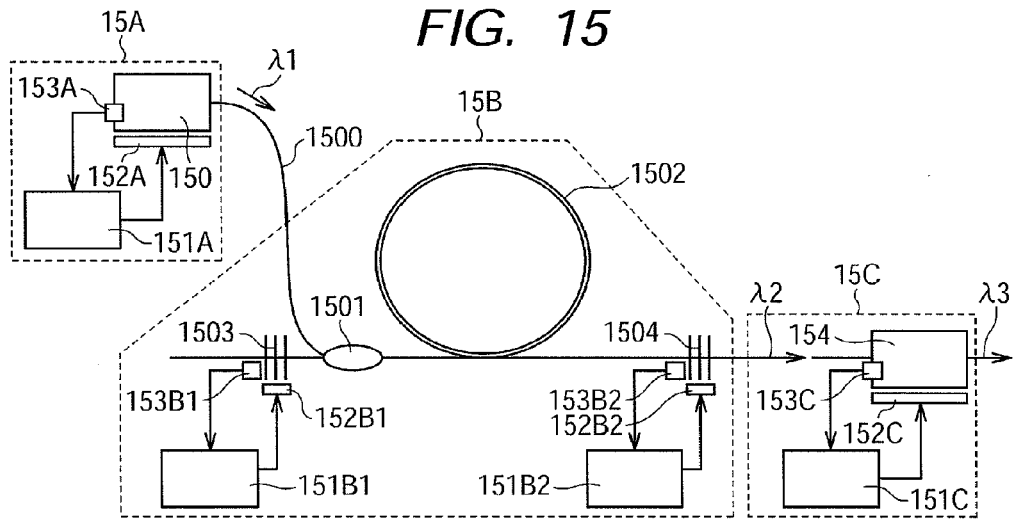
FIG. 15 shows a first example of a mechanism which changes a wavelength of the illumination light source.

FIG. 15 shows a first example of a mechanism which changes the wavelength of the illumination light source. Reference number 15A denotes a seed laser section, 15B an amplifier section, and 15C a wavelength converter section. Reference number 150 denotes a laser diode (LD), 1500 a passive fiber, 1501 a coupling, and 1502 an amplifying fiber. Reference numbers 1503B1 and 1503B2 denote fiber Bragg gratings (FBGs). Reference number 154 denotes a nonlinear optical crystal.

Referring to the seed laser section 15A, laser light with a wavelength λ1 is emitted from the LD 150 and introduced into the amplifier section 15B via the passive fiber 1500.

Referring to the amplifier section 15B, the amplifying fiber 1502 is an optical fiber doped with rare earthes, and the FBGs 1503B1, 1503B2 placed across the amplifying fiber 1502 function as diffraction gratings to generate periodic variations in the refractive index of the passive fiber 1500. Thus, only wavelengths that satisfy a Bragg reflection condition created by a period of the gratings are reflected, which forms an optical cavity, amplifies the incident λ1 laser light, then emits λ2 laser light, and admits the λ2 laser light into the wavelength converter section 15C.

Referring to the wavelength converter section 15C, the nonlinear optical crystal 154 includes a barium borate (BBO) crystal (βBaB2O4), a lithium triborate (LBO) crystal (LiB3O5), a KTP crystal (KTiOPO4), and a lithium niobate crystal (LiNbO3). The nonlinear optical crystal 154 receives the incident λ2 laser light and emits high-harmonic λ3 laser light. With this configuration, high-power and short-wavelength laser light can be emitted.

In the other constituent elements in FIG. 15, 151A, 151B1, 151B2, 151C are temperature control units, and the temperature control elements 152A, 152B1, 152B2, 152C are Peltier elements or heaters. Temperature sensors 153A, 153B1, 153B2, 153C work to sense temperature states of various constituent elements and send information to the corresponding temperature control units 151A-151C, and the temperature control units 151A-151C control the temperature control element 152A and corresponding temperature control elements 152B, 152C to maintain the various constituent elements at required temperatures.

The LD 150, FBGs 1503, 1504, and nonlinear optical crystal 154 here have a characteristic in that each changes a corresponding wavelength according to temperature. In the LD 150, for example, when the element increases in temperature, the wavelength of the laser light emitted will shift to a greater wavelength. This also occurs in the FBGs 1503, 1504. When the FBG increases in temperature, thermal expansion spreads a spacing of its diffraction gratings and the Bragg wavelength shifts to a greater wavelength. In addition, an increase in a temperature of the nonlinear optical crystal 154 causes a change in its refractive index, thus shifting the wavelength of the higher-harmonic light.

These characteristics can be used to shift the wavelength of the illumination light source depicted in the overall block diagram of FIG. 15, by controlling the temperatures of the constituent elements. This feature, in turn, can be used to correct the lens characteristics for an environmental change.

Figure 16:
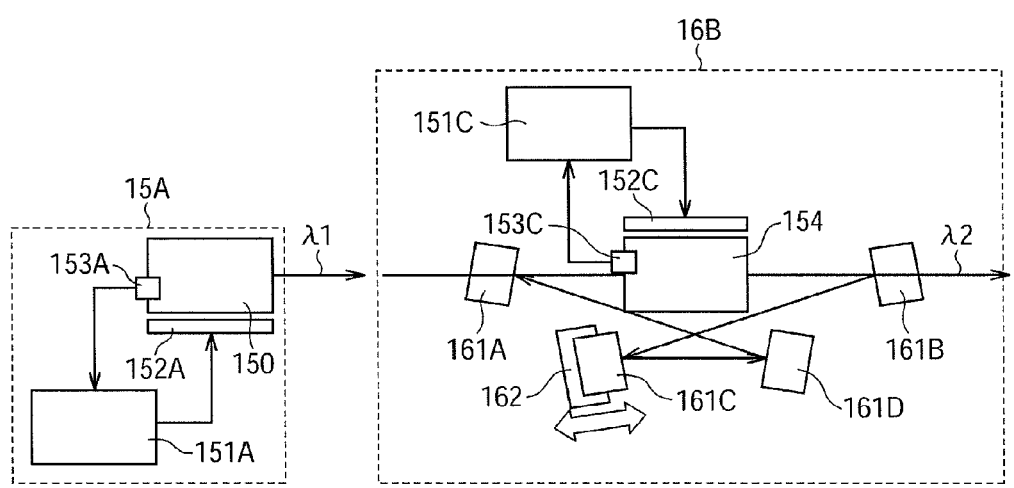
FIG. 16 shows a second example of a mechanism which changes the wavelength of the illumination light source.

FIG. 16 shows a second example of a mechanism which changes the wavelength of the illumination light source. Detailed description of constituent elements assigned the same reference numbers as in FIG. 15 is omitted herein.

In the present example, the laser light of a λ1 wavelength that has been emitted from the seed laser section 15A is admitted into a wavelength converter section 16B. The wavelength converter section 16B activates the nonlinear optical element 154 to form an optical cavity via mirrors 161A, 161B, 161C, 161D, on the optical path. In this configuration, the nonlinear optical element 154 is temperature-controlled by the temperature control unit 151C, the temperature control element 152C, and the temperature sensor 153C, and the mirror 161C is moved by a mirror actuator mechanism 162. These actions change cavity length and thus allow wavelength shifting of the λ2-wavelength laser light which has been emitted from the wavelength converter section 16B. This feature can be further used to correct the lens characteristics for an environmental change.

Third Embodiment

A third embodiment relates to a direction of illumination. As described earlier herein, the present embodiment presupposes that the longitudinal direction of the thin linear illumination region 1000 is set to be the y-axis direction, but this is not intended to limit the direction of the illumination.

Constituent elements of the present embodiment, such as the illumination optics unit 10 and the detection optics system 11, are substantially the same as in the defect inspection device of the first embodiment described using FIG. 1, and the present (third) embodiment differs from the first embodiment in terms of a location of the illumination optics unit 10 relative to the detection optics system 11.

As shown in FIG. 11, a plane 1010, formed by a line 1111 normal to a surface of a wafer 001 and an optical axis of the illumination light, may have an arbitrary azimuth angle "φi" with respect to the y-axis. Thus, as described earlier herein, different scattered-light components will enter the detection optical units arranged to be left-right symmetrical with respect to the normal 1111 to the surface of the wafer 001, and detection sensitivity will thus improve.

Figure 12:
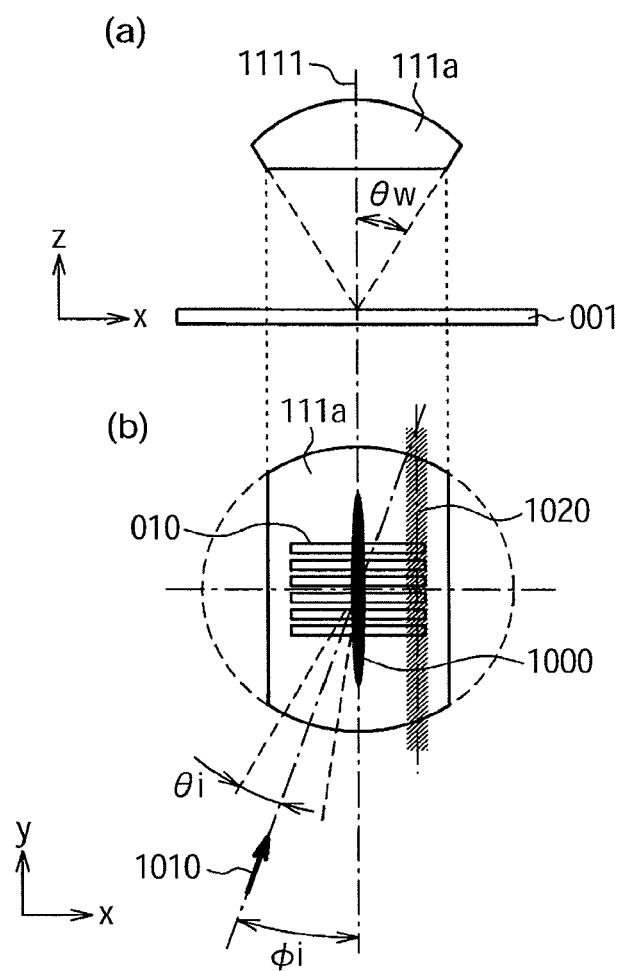
FIG. 12 is a front view (a) representing a relationship between the patterned substrate to be inspected and an objective lens of a detection unit, and a plan view (b) representing a relationship between the patterned substrate that has been illuminated with a thin linear beam of light, and the objective lens of the detection unit.

The section (a) of FIG. 12 is a front view representing a relationship between the patterned substrate to be inspected and an objective lens of the detection optics system, and the section (b) of FIG. 12 is a plan view representing a relationship between the patterned substrate that has been illuminated with a thin linear beam of light, and the objective lens of the detection optics system.

However, as shown in the section (a) of FIG. 12, when the objective lens 111a having the same optical axis as the normal 1111 to the surface of the wafer 001 is placed, it is effective to set "φi" in a limited range so that as shown in the section (b) of FIG. 12, diffracted light 1020 from a circuit pattern 010 extending in parallel in an x-direction on the wafer will enter the objective lens 111a.

The reason for this is described below. In the present embodiment, the second and third detection units described in FIG. 1 but not shown in FIG. 12 are arranged to be left-right symmetrical with respect to the normal 1111 to the surface of the wafer 001, and these detection units detect substantially the same scattered-light images. The scattered-light images that the detection units have thus acquired reflect only a difference in the direction of the scattered light. The present embodiment assumes highly sensitive detection of a defect by comparing these images of the scattered light. If the diffracted light 1020 from the circuit pattern 010 enters at least one of objective lenses 111b, 111c of the second and third detection units, however, a significant difference will occur between the two images of the scattered light, and this difference will make it impossible to compare the scattered-light images that reflect only the difference in the direction of the scattered light.

This, in turn, makes it necessary to conduct the illumination so that an illumination converging angle "θi", the illumination azimuth angle "φi" with respect to the longitudinal direction (y-axis) of the linear illumination in the object plane, and a detection angle "θW" of the first detection optics system having the same optical axis as the normal to the object surface, with respect to a direction perpendicular to the rectilinear portion of the lens, that is, in the section (b) of FIG. 12, the x-direction, will satisfy a relation of φi≤θw−θi.

REFERENCE SIGNS LIST

001 . . . wafer 01 . . . total control unit 10 . . . illumination optics unit 101 . . . light source 102 . . . polarization state controller 103 . . . beam-forming unit 104 . . . thin-line converging optics system 1000 . . . thin linear illumination region 11 . . . detection optics unit 11a,11b,11c . . . detection unit 111a,111b,111c . . . objective lens 112a,112b,112c . . . spatial filter 113a,113b,113c . . . polarization filter 114a, 114b,114c . . . imaging lens 115a,115b,115c . . . image sensor 12 . . . data-processing unit 121a,121b,121c . . . signal-processing unit 122 . . . image-processing unit 13 . . . stage unit

What is claimed is:

1. A defect inspection device, comprising:
an irradiation unit that irradiates a surface-patterned sample with light from an inclined direction relative to the surface of the sample;
a detection unit that includes a plurality of detection optical systems to detect respectively a plurality of portions of scattered light coming from the surface of the sample irradiated with light by the irradiation unit; and
a processing unit that processes a plurality of signals based on the plurality of the portions of the scattered light detected respectively by the plurality of the detection optical systems in the detection unit,
wherein:
the detection unit detects the plurality of the portions of the scattered light using the plurality of the detection optical systems including, at least, a first detection optical system including a detector placed in a normal direction relative to the surface of the sample, a second detection optical system including a detector placed in a direction at an elevation angle relative to the surface of the sample different from an elevation angle at which the first detection optical system is located, and a third detection optical system including a detector placed in a direction at an elevation angle relative to the surface of the sample different from the elevation angles at which the first detection optical system and the second detection optical system are located; and
the processing unit evaluates, relative to a first signal based on the first portion of the scattered light detected by the first detection optical system, a second signal based on the second portion of the scattered light detected by the second detection optical system and a third signal based on the third portion of the scattered light detected by the third detection optical system in order to detect a defect.

2. The defect inspection device according to claim 1, wherein the processing device uses a difference between the first signal and the second signal and a difference between the first signal and the third signal to perform the evaluation.

3. The defect inspection device according to claim 1, wherein a difference between an angle of the first detection optical system with respect to the surface of the sample and an angle of the second detection optical system with respect to the surface of the sample is approximately equal to a difference between the angle of the first detection optical system with respect to the surface of the sample and an angle of the third detection optical system with respect to the surface of the sample.

4. The defect inspection device according of claim 1, wherein, for the detection of images of the portions of the scattered light coming from the sample which are detected by the plurality of the detection optical systems, a degree of matching in quality of each of the images is calibrated in response to a temperature environment and an atmospheric pressure environment of a position at which the sample is inspected.

5. The defect inspection device according to claim 4, wherein the degree of matching in quality of each of the images is calibrated by controlling a spacing between an imaging lens used to form the images of the scattered light, and image sensors that detect the scattered-light images formed by the imaging lens.

6. The defect inspection device according to claim 4, wherein the degree of matching in quality of each of the images is calibrated by moving at least one of a plurality of lenses of a lens system that form the images of the scattered light, in relative fashion with respect to an optical-axis direction of the lens system.

7. The defect inspection device according to claim 1, wherein detecting images of the scattered light by the plurality of detection optical systems is performed through oval shaped lenses in which elevation angles of the optical axes thereof are different from each other, within one plane perpendicular to a plane formed by the normal to a surface of a table on which to mount the sample and a longitudinal direction of a linear region irradiated with the irradiation light, each of the oval shaped lenses being formed of a circular lens having left and right portions thereof cut.

8. A defect inspection method, comprising:
  irradiating a surface-patterned sample with light from an inclined direction relative to the surface of the sample;
  detecting a plurality of portions of scattered light coming from the surface of the sample irradiated with light in the irradiating, by a plurality of detection optical systems, respectively; and
  processing a plurality of signals based on the plurality of the portions of the scattered light detected respectively by the plurality of the detection optical systems in the detecting,
  wherein:
    in the detecting, the plurality of the portions of the scattered light are detected by the plurality of the detection optical systems including, at least, a first detection optical system including a detector placed in a normal direction relative to the surface of the sample, a second detection optical system including a detector placed in a direction at an elevation angle relative to the surface of the sample different from an elevation angle at which the first detection optical system is located, and a third detection optical system including a detector placed in a direction at an elevation angle relative to the surface of the sample different from the elevation angles at which the first detection optical system and the second detection optical system are located; and
    in the processing, relative to a first signal based on the first portion of the scattered light detected by the first detection optical system, a second signal based on the second portion of the scattered light detected by the second detection optical system and a third signal based on the third portion of the scattered light detected by the third detection optical system are evaluated in order to detect a defect.

9. The defect inspection method according to claim 8, wherein, in the processing, a difference between the first signal and the second signal, and a difference between the first signal and the third signal are used to perform the evaluation.

10. The defect inspection method according to claim 8, wherein a difference between an angle of the first detection optical system with respect to the surface of the sample and an angle of the second detection optical system with respect to the surface of the sample is approximately equal to a difference between the angle of the first detection optical system with respect to the surface of the sample and an angle of the third detection optical system with respect to the surface of the sample.

11. The defect inspection method according of claim 8, further comprising:
  detecting images of the portions of the scattered light coming from the sample which are detected by the plurality of the detection optical systems, by calibrating a degree of matching in quality of each of the images, in response to a temperature environment and atmospheric pressure environment of a position at which the sample is inspected.

12. The defect inspection method according to claim 11, wherein the degree of matching in quality of each of the images is calibrated by controlling a spacing between an imaging lens used to form the images of the scattered light, and image sensors that detect the scattered-light images formed by the imaging lens.

13. The defect inspection method according to claim 11, wherein the degree of matching in quality of each of the images is calibrated by moving at least one of a plurality of lenses of a lens system that form the images of the scattered light, in relative fashion with respect to an optical-axis direction of the lens system.

14. The defect inspection method according to claim 8, wherein detecting images of the scattered light by the plurality of detection optical systems is performed through oval shaped lenses in which elevation angles of the optical axes thereof are different from each other, within one plane perpendicular to a plane formed by the normal to a surface of a table on which to mount the sample and a longitudinal direction of a linear region irradiated with the irradiation light, each of the oval shaped lenses being formed of a circular lens having left and right portions thereof cut.

* * * * *